United States Patent [19]

Green et al.

[11] Patent Number: 4,508,743

[45] Date of Patent: * Apr. 2, 1985

[54] CAFFEINE ADSORPTION

[75] Inventors: David Green, Chavornay; Maurice Blanc, Morges, both of Switzerland

[73] Assignee: Societe d'Assistance Technique pour Produits Nestle S.A., Lausanne, Switzerland

[*] Notice: The portion of the term of this patent subsequent to Jan. 22, 2002 has been disclaimed.

[21] Appl. No.: 264,062

[22] Filed: May 15, 1981

Related U.S. Application Data

[63] Continuation-in-part of Ser. No. 153,904, May 28, 1980.

[51] Int. Cl.³ ............................................. A23F 5/22
[52] U.S. Cl. ..................................... 426/422; 426/427
[58] Field of Search ............................... 426/422, 427

[56] References Cited

U.S. PATENT DOCUMENTS 2,198,859  4/1940  Bürgin ............................ 426/427 X
4,160,042  7/1979  Farr et al. ....................... 426/427 X

OTHER PUBLICATIONS

Hassler, Active Carbon, 1951, Chemical Publ. Co., Inc., New York, pp. 21, 184, 358–360.
Hassler Purification with Active Carbon–Industrial Commercial Environmental, Chemical Publ. Co., New York, pp. 34, 37, 91, 182–183, 346–348.

*Primary Examiner*—Joseph Golian
*Attorney, Agent, or Firm*—Vogt & O'Donnell

[57] ABSTRACT

In the decaffeination of green coffee beans with an aqueous medium, caffeine is removed from the aqueous medium which also contain non-caffeine green coffee solids, contact with substantially neutral active carbon. Thereafter the medium may be recycled to extract further amounts of caffeine from the same or another batch of green coffee beans.

Other features of the invention are described in the specification.

3 Claims, No Drawings

CAFFEINE ADSORPTION

This is a continuation-in-part of application Ser. No. 153,904, filed May 28, 1980.

This invention is concerned with the recovery of caffeine from aqueous media.

In the preparation of decaffeinated coffee, two basic approaches are available for the extraction of caffeine from the beans. According to the first, green (unroasted) coffee beans are extracted with water or an aqueous solution containing non-caffeine green coffee solids, the aqueous extract is separated from beans, caffeine is removed from the extract, usually by solvent extraction or adsorption on a solid adsorbent and the caffeine-free extract may be returned to the coffee beans. The second approach involves direct contact between the beans and the caffeine solvent, usually methylene chloride, and evaporation of the solvent leaving behind the caffeine. Of the various solid adsorbents that have been proposed, activated carbon offers certain advantages over substances such as polymeric resins because of its ready availability and ease of regeneration. However, it has been observed that contact between the aqueous extract and active carbon frequently leads to an increase of pH which is associated with a deterioration in the colour and flavour of the coffee beans.

It has now been found that the undesirable increase of pH may be considerably diminished if the activated carbon used shows a substantially neutral reaction on dispersion in water.

The invention thus provides a process for the recovery of caffein from an aqueous solution containing caffeine extracted from green coffee beans and non-caffeine green coffee solids, which comprises contacting the solution with substantially neutral activated carbon and separating the activated carbon, with caffeine adsorbed thereon, from aqueous solution of reduced caffeine content. The term "substantially neutral" used to describe the activated carbon means that when the carbon is immersed in water the pH value is substantially unchanged. Carbon having this property may be obtained either by acid washing or thermally activated carbon followed by rinsing with water to neutrality, or by neutralisation of acid-activated carbon with an aqueous alkali followed by rinsing with water to neutrality.

The aqueous caffeine solution is obtained by conventional methods, involving contact of green coffee beans with water for a period time sufficient to reduce the caffeine content of the beans to the desired level. The contacting may be effected in a counter-current system, using an arrangement similar to those used for extracting roasted coffee in the preparation of coffee extract, or batch contact may be employed wherein a fixed volume of water is continuously recycled to a fixed weight of coffee beans, caffeine being removed from the extract at each cycle prior to its being returned to the beans. In the counter-current system, the aqueous extraction medium containing caffeine and non-caffeine green coffee solids encounters coffee of progressively higher caffeine content. On leaving the system, the caffeine-laden extract is contacted with the adsorbent, preferably again in a counter-current column system. The main factors affecting the operation are temperature, the ratio of extraction liquid to coffee, the ratio of carbon to coffee, time and liquid velocity, each of which may be adapted to the degree of decaffeination desired. In carrying out the process according to the invention, the neutral activated carbon may be used either in the batch or the counter-current continuous system. In both cases provision is usually made for continuity of operation by duplicating the beds of adsorbent so that one or more may be renewed whilst the others are on stream.

Decaffeination of green coffee beans is preferably effected with deionised water; the water to coffee ratio is by no means critical, but rather is determined having regard to practical considerations imposed by industrial operations. Excessive volumes are thus avoided, as also water to coffee ratios which do not provide for adequate caffeine extraction. It has been found that in general a weight ratio of water to green coffee of at least about 3 parts of water per part of coffee gives satisfactory results.

In one preferred embodiment, green coffee beans are contacted as a static bed, in a column, or in a suitable tumbler or like extractor. In both cases, the weights of coffee and water are constant, with the caffeine-laden water withdrawn from the column or extractor being decaffeinated with neutral activated carbon prior to its being recycled. The weight of carbon is usually 20 to 30% of the weight of green coffee being decaffeinated. The total contact time will depend, inter alia, on the water/coffee ratio, temperature and the degree of decaffeination desired. In most cases it is 3 to 10 hours. The temperature is preferably in the range of 60° to 90° C. Lower temperatures are usually avoided as the risk of microbial growth, especially with long contact times, is increased, resulting in fermentation of the sugars present in the extract. In addition, the rate of caffeine diffusion from the beans decreases with temperature. Above 90° C., with long contact times, flavour may be impaired and as a practical matter it is difficult to maintain these temperatures without resort to pressurised equipment.

In another preferred embodiment of the invention, applied to continuous extraction and decaffeination of green coffee beans, a counter-current system is used.

The green coffee is extracted using an arrangement similar to those used for extracting roasted coffee. The fresh water entering the most exhausted extractor is normally at a temperature in the range 90° to 120° C. Deionised water is used for preference. The water to coffee ratio is not critical but is generally between 3:1 and 15:1 by weight. The number of extractors and cycle time are chosen to give the desired degree of decaffeination. Up to eight extractors, in series, may be used with a cycle time of between 15 and 120 min.

The aqueous extract containing caffeine and non-caffeine green coffee solids may be concentrated before being decaffeinated by contacting with neutralised, activated carbon, but preferably it has a solids content not exceeding 10% by weight. Contacting may be effected in a counter-current system with several columns of carbon and the extract passing serially through the columns. Periodically the most saturated column is removed from the system and one containing fresh carbon added. The temperature in the columns is preferably between 60° and 90° C. The number of columns, the cycle time for each column and the residence time of the extract are chosen to achieve the degree of decaffeination desired and to minimise the quality of carbon used. The weight of carbon is usually 10-20% of the total of green coffee being decaffeinated.

In the batch/recirculation system, contact temperature between carbon and extract should desirably be at least about 60° C. to avoid microbiological problems, whereas in a column arrangement the inlet temperature should be a little higher for the same reason. No well-defined relationship between temperature and caffeine adsorption has been observed.

Since the activated carbon adsorbs acid as well as caffeine, the pH of the aqueous extract rises, reaching a maximum of 6.0 to 7.5. However, as the operation proceeds, the pH falls again so that when, for example, 97% decaffeination is attained, it has risen by less than 1 unit over the natural pH of an aqueous green bean extract. In contrast, the pH of a green bean extract contacted with non-neutralised activated carbon rises to above 9.0, which possibly explains the deterioration in colour and flavour.

By way of illustration, the results obtained when different activated carbons are employed in the batchwise manner described above are given below. A deionised water/coffee ratio of 4:1 by weight is used, 24% carbon based on the weight of green coffee and the temperature of the system maintained at 70° C. during 8 hours.

| Carbon | pH of carbon in distilled water at 20° C. | Max. pH of extract at 20° C. | Final pH of extract at 20° C. |
|---|---|---|---|
| A. Thermally activated, non-neutralised | | | |
| A1 | 10.8 | 9.4 | 7.2 |
| A2 | 11.2 | 9.6 | 7.0 |
| A3 | 9.5 | 9.5 | 7.1 |
| B. Thermally activated, neutralised | | | |
| B1 | 7.5 | 6.7 | 6.2 |
| B2 | 7.7 | 6.2 | 5.9 |
| B3 | 8.5 | 7.5 | 6.1 |
| B4 | 7.4 | 6.5 | 5.5 |
| C. Acid activated neutralised | | | |
| C1 | 6.2 | 6.5 | 6.4 |

When decaffeination is terminated, it is usually desirable, to avoid excessive losses, to return the non-caffeine solids present in the aqueous extract to the decaffeinated green beans. Various techniques may be used. For example, the beans may be pre-dried, usually to 10–45% by weight moisture and combined directly with the extract. Alternatively the extract may be pre-concentrated, e.g. by evaporation, to a solids content of 15–55% by weight before contact with the beans. Satisfactory reincorporation of the solids is obtained in 4 to 8 hours, preferably at 60°–80° C. Desirably, the total amount of water present is such that the final moisture content of the beans does not exceed about 55% by weight. The "total" water is made up of the residual moisture of the pre-dried beans and the water present in the aqueous extract. After reincorporation of solids the coffee is dried to a moisture content of 5–12% by weight before being roasted. In a modification, the amount of non-caffeine solids contacted with the coffee beans may be less than the amount extracted during decaffeination.

Periodically the active carbon may be regenerated, usually by heating or solvent extraction.

The invention is illustrated by the following Examples, in which all parts, ratios and percentages are expressed on a weight basis unless otherwise stated.

EXAMPLE 1

Neutralised activated carbon is prepared by washing commercial thermally activated carbon with 2% hydrochloric acid followed by rinsing with deionised water (pH=6.0) until the pH of the washings is constant at 6.0. 2000 parts of green coffee beans are loaded into a tumbler extractor together with 7000 parts of deionised water. The temperature is raised to (and maintained at) 80° C. Solution is withdrawn from the extractor and recirculated at a rate of 15000 parts/hour, passing through a column containing 230 parts of the neutralised activated carbon, before returning to the extractor. After one hour, a second column also containing 230 parts of neutralised activated carbon is connected in series with the first.

After 5 hours' total operation, recirculation is stopped and the extract, having a pH of 6.2, is separated from the beans. The beans are dried to 20% moisture and mixed with the extract, which has first been concentrated to 20% solids. Mixing is continued for 6 hours at 65° C. Thereafter, the coffee, containing 45% moisture, is dried to a 8.5% moisture content.

The coffee is 97% decaffeinated and has a good appearance, similar to the original, non-decaffeinated beans but somewhat darker in colour. When roasted and prepared as an infusion, the brew is described by a panel of trained tasters as being of good quality and colour. When milk is added to the cup, the brew assumes a red-brown colour, without traces of greyness.

EXAMPLES 2 TO 4

The coffee decaffeination procedure described in Example 1 is repeated with various modifications in materials and operating parameters. The results are summarised in Table I.

TABLE I

| Ex. | pH of* carbon | Water/ coffee ratio | Carbon as % of coffee | Temp. °C. | Total time hours | Extract final pH | % Decaff. of coffee |
|---|---|---|---|---|---|---|---|
| 1 | 7.5 | 3.5 | 23 | 80 | 5 | 6.2 | 97 |
| 2 | 7.5 | 3.5 | 23 | 65 | 7 | 6.2 | 97 |
| 3 | 7.5 | 3.5 | 23 | 80 | 5 | 6.0 | 97 |
| 4 | 7.4 | 4.0 | 25 | 65 | 8 | 5.5 | 97 |

*measured in distilled water at 20° C.

After decaffeination, the non-caffeine solids are combined with the decaffeinated beans.

EXAMPLE 5

Green coffee beans are decaffeinated continuously by counter-current extraction with an aqueous solution. 6 extractors in series are used, each containing 60 kg of green coffee. Extraction is carried out with deionised water at 100° C. entering the most exhausted extractor. An aqueous solution containing caffeine and non-caffeine green bean solids is removed at 80° C. from the extractor containing the least exhausted coffee. The last extractor containing decaffeinated coffee is removed from the system and one containing fresh green coffee beans added once per hour. The ratio of water to green coffee beans is 10:1 so that the flow rate of water entering the system is 600 lt/hr.

The extract coming from the least exhausted green coffee is passed counter-currently through 3 columns in series, each column containing 35 kg of neutralised, activated carbon prepared in a manner similar to that described in Example 1. The temperature in the columns is maintained at 75° C. The most saturated carbon column is removed and a fresh one added every four hours.

The decaffeinated green beans are dried to 20% moisture and mixed with the corresponding quantity of decaffeinated extract, which has first been concentrated to 20% solids. Mixing is continued for 6 hours at 75° C. Thereafter, the coffee containing 45% moisture is dried to 9.0% moisture content.

Table II summarises the results of tasting by a trained panel of beverages obtained from coffee decaffeinated in accordance with Examples 1, 2 and 5 and roasted. These coffees are compared to coffees decaffeinated in a manner similar to that described in Example 1, but using the carbon employed in Example 1 which has not been acid neutralised and which gives a pH of 10.8 in distilled water (A) and a carbon which gives a pH of 9.5 in distilled water (B).

TABLE II

| Ex. | pH of* carbon | Aroma | Taste | Colour + milk | Rank | Hedonic scale |
|---|---|---|---|---|---|---|
| 1 | 7.5 | Good, fresh | Good, full clean, balanced | Red brown | 3 | 6.9 |
| 2 | 7.5 | Good, full | Good, acid clean, flavoury | Red brown | 1 | 7.1 |
| 5 | 7.5 | Fresh, aromatic | Natural, clean, mild, balanced | Red brown | 1 | 7.1 |
| A | 10.8 | Weak | Sl. nutty, harsh, acid, papery | Grey brown | 4 | 4.2 |
| B | 9.5 | Sl. nutty, Sl. bready | Aggressive, sl. nutty, old | Greyish brown | 5 | 4.1 |

*measured in distilled water at 20° C.

We claim:

1. A process for the removal of caffeine from green coffee beans which comprises contacting the beans with an aqueous medium selected from the group consisting of water, an aqueous solution of non-caffeine green coffee solids and an aqueous solution of non-caffeine green coffee solids containing a minor amount of caffeine, recovering aqueous medium containing caffeine dissolved from the green coffee beans, removing caffeine from the medium by contact with substantially neutral activated carbon, separating the activated carbon with caffeine adsorbed thereon from aqueous medium of reduced caffeine content and combining non-caffeine green coffee solids present in the aqueous medium of reduced caffeine content with green coffee beans having a reduced content of caffeine and of non-caffeine green coffee solids, the ratio of aqueous medium to green coffee beans being 3:1 to 15:1.

2. A process for the removal of caffeine from green coffee beans which comprises contacting the beans with an aqueous medium selected from the group consisting of water, an aqueous solution of non-caffeine green coffee solids and an aqueous solution of non-caffeine green coffee solids containing a minor amount of caffeine, recovering aqueous medium containing caffeine dissolved from the green coffee beans, removing caffeine from the medium by contact with substantially neutral activated carbon, separating the activated carbon with caffeine adsorbed thereon from aqueous medium of reduced caffeine content and combining non-caffeine green coffee solids present in the aqueous medium of reduced caffeine content with green coffee beans having a reduced content of caffeine and of non-caffeine green coffee solids, the aqueous medium containing caffeine contacted with activated carbon having a solids content not exceeding 10% by weight.

3. A process according to claim 1 or claim 2 in which the caffeine content of the aqueous medium is reduced substantially to zero.

* * * * *

UNITED STATES PATENT AND TRADEMARK OFFICE
CERTIFICATE OF CORRECTION

PATENT NO. : 4,508,743
DATED : April 2, 1985
INVENTOR(S) : David Green, et al.

It is certified that error appears in the above—identified patent and that said Letters Patent is hereby corrected as shown below:

Column 1, line 34, "caffein" should read --caffeine--.

Column 1, line 44, "or" should read --of--.

Column 2, line 68, "total" should read --weight--.

Column 3, line 8, "acid" should read --acids--.

Signed and Sealed this

Sixteenth Day of July 1985

[SEAL]

Attest:

DONALD J. QUIGG

Attesting Officer  Acting Commissioner of Patents and Trademarks